US006838681B2

(12) United States Patent
Mayolet et al.

(10) Patent No.: US 6,838,681 B2
(45) Date of Patent: Jan. 4, 2005

(54) DETECTION AND MAKING OF ULTRALOW LEAD CONTAMINATED UV OPTICAL FLUORIDE CRYSTALS FOR <200NM LITHOGRAPHY

(75) Inventors: Alexandre M. Mayolet, Auneau (FR); Nikolay T. Timofeev, St. Petersburg (RU)

(73) Assignee: Corning Incorporated, Corning, NY (US)

( * ) Notice: Subject to any disclaimer, the term of this patent is extended or adjusted under 35 U.S.C. 154(b) by 106 days.

(21) Appl. No.: 10/317,920

(22) Filed: Dec. 11, 2002

(65) Prior Publication Data

US 2004/0026631 A1 Feb. 12, 2004

(30) Foreign Application Priority Data

Aug. 12, 2002 (RU) .................................. RU2002121259

(51) Int. Cl.[7] .............................................. G01N 21/64
(52) U.S. Cl. ................... 250/461.1; 250/458.1
(58) Field of Search ........................... 250/461.1, 458.1

(56) References Cited

U.S. PATENT DOCUMENTS

| 4,101,331 A | * | 7/1978 | Anderson .................... 501/151 |
| 4,562,356 A | | 12/1985 | Auth ........................ 250/458.1 |
| 6,226,128 B1 | | 5/2001 | Shiozawa .................... 359/642 |
| 6,486,949 B2 | * | 11/2002 | Hachfeld et al. ............ 356/318 |
| 2002/0132719 A1 | * | 9/2002 | Mayolet et al. ................ 501/3 |
| 2003/0160177 A1 | * | 8/2003 | Mayolet et al. ............. 250/372 |

FOREIGN PATENT DOCUMENTS

| WO | WO 01/86032 A1 | * 11/2001 | ........... C30B/11/00 |
| WO | WO 03/052392 A1 | * 9/2003 | ........... G01N/21/59 |

* cited by examiner

*Primary Examiner*—David Porta
*Assistant Examiner*—Christine Sung
(74) *Attorney, Agent, or Firm*—Walter M. Douglas

(57) ABSTRACT

The invention provides a method of detecting sub-ppm lead impurity levels in a below 200 nm transmitting optical calcium fluoride crystal. The method includes providing a below 200 nm wavelength transmitting optical calcium fluoride crystal, providing a fluorescence spectrometer having a light source for producing a 200 to 210 nm selectable wavelength incident radiation and a detector for detecting excited luminescence light in the wavelength range of 210–260 nm produced by the incident radiation, exciting a first luminescence area of the crystal with the 200 to 210 nm selectable wavelength incident radiation and detecting with the detector excited 210 to 260 luminescence light produced from the crystal luminescence area by the 200 to 210 incident radiation to provide a lead ppb impurity level measurement less than 100 ppb. The invention provides for improved manufacturing of below 200 nm wavelength optical elements and optical fluoride crystals such as ultralow lead contaminated calcium fluoride.

26 Claims, 18 Drawing Sheets

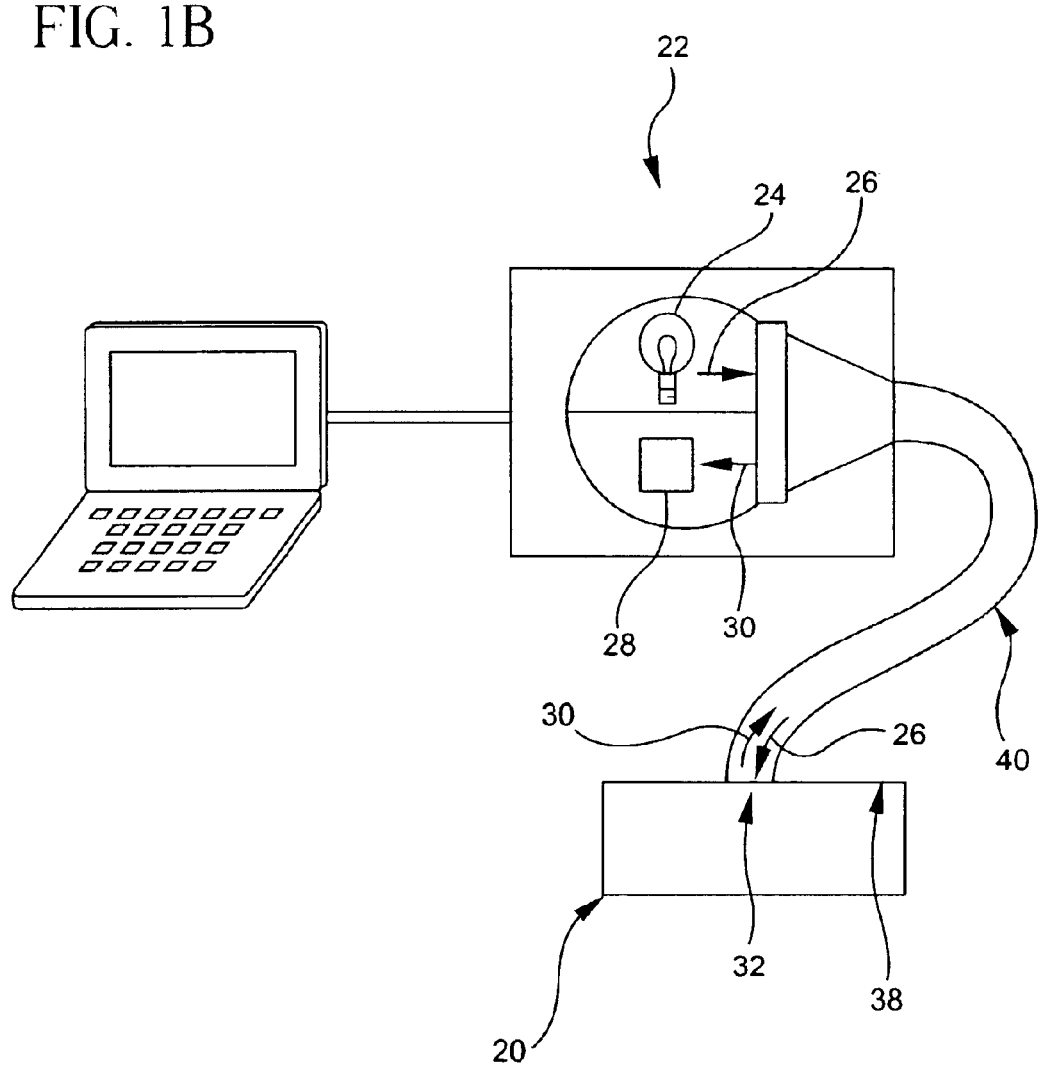

DETECTION AND MAKING OF ULTRALOW LEAD CONTAMINATED UV OPTICAL FLUORIDE CRYSTALS FOR <200NM LITHOGRAPHY

RELATED APPLICATIONS

This application claims the priority of Russian Patent Application, Serial No. RU2002121259, filed Aug. 12, 2002 entitled DETECTION AND MAKING OF ULTRALOW LEAD CONTAMINATED UV OPTICAL FLUORIDE CRYSTALS FOR <200 NM LITHOGRAPHY.

BACKGROUND OF THE INVENTION

The present invention relates generally to UV transmitting optical fluoride crystals and optical elements therefrom, and particularly to the evaluating and making high quality calcium fluoride optical fluoride crystals and lithography/laser elements with very low contaminant level measured impurity luminescent concentrations such as lead with luminescence analysis.

The burden of the demands for improved performance of computers falls on the lithographic process used to fabricate the integrated circuit chips. Lithography involves irradiating a mask and focusing the pattern of this mask through an optical microlithography system onto a wafer coated with a photoresist. The pattern on the mask is thereby transferred onto the wafer. Decreasing the line-widths of the features on a given wafer brings about advances in performance. The enhanced resolution required to achieve finer line-widths is enabled by decreasing the wavelength of the illumination source. The energies used in lithographic patterning are moving deeper into the UV region. Optical components capable of reliable performance at these short optical microlithography wavelengths are required. Few materials are known that have a high transmittance at 193 nm and 157 nm and do not deteriorate under intense laser exposure. Fluoride crystals such as calcium fluoride and barium fluoride are potential materials with high transmittance at wavelengths <200 nm. Projection optical photolithography systems that utilize the vacuum ultraviolet wavelengths of light at and below 193 nm provide desirable benefits in terms of achieving smaller feature dimensions. Microlithography systems that utilize vacuum ultraviolet wavelengths in the 157 nm wavelength region have the potential of improving integrated circuits and their manufacture. The commercial use and adoption of 193 nm and below vacuum ultraviolet wavelengths such as 157 nm has been hindered by the transmission nature of such deep ultraviolet wavelengths in the 157 nm region through optical materials. Such slow progression by the semiconductor industry of the use of VUV light below 175 nm such as the 157 nm region light has been also due to the lack of economically manufacturable blanks from optically transmissive materials and difficulties in manufacturing blanks which can be identified as high quality and qualified for their intended microlithography optical element and laser use. For the benefit of deep ultraviolet photolithography in the VUV 157 nm region such as the emission spectrum of the fluorine excimer laser to be utilized in the manufacturing of integrated circuits there is a need for below 200 nm wavelength transmitting optical fluoride crystals that have beneficial optical and highly qualified properties including good transmission below 200 nm and at 193 nm and 157 nm and that can be manufactured, tested, evaluated, measured and qualified for use economically. The present invention overcomes problems in the prior art and provides a means for economically providing high quality very low contaminant level measured for below 200 nm wavelength transmitting optical fluoride crystals that can be used to improve the manufacturing of integrated circuits with vacuum ultraviolet wavelengths. The invention provides for luminescence analysis of high quality calcium fluoride optical fluoride crystal lithography and excimer laser elements with very low contaminant level concentrations of impurities such as lead.

SUMMARY OF THE INVENTION

The invention includes a method of detecting sub-ppm lead impurity levels in below 200 nm transmitting optical calcium fluoride crystals. The method includes providing a below 200 nm wavelength transmitting optical calcium fluoride crystal with a lead level less than 1 ppm. The method includes providing a fluorescence spectrometer with a light source for producing 200 to 210 nm selectable wavelength incident radiation and a detector for detecting excited luminescence light in the wavelength range of 210–260 nm produced by the incident radiation. The method includes exciting a first luminescence area of the crystal with the 200 to 210 nm selectable wavelength incident radiation and detecting with the detector excited 210 to 260 nm luminescence light produced from the crystal luminescence area by the 200 to 210 nm incident radiation to provide a lead ppb impurity level measurement less than 100 ppb by weight for the crystal luminescence area.

The invention includes a method of measuring below 1 ppm impurity levels in an optical fluoride lithography crystal for transmitting below 200 nm wavelengths of light. The method includes providing a fluorescence spectrometer for providing a selectable wavelength incident radiation greater than 200 nm and detecting excited luminescence light produced by the incident radiation. The method includes providing an optical flu crystal for transmitting below 200 nm wavelengths of light with the crystal containing an impurity at a contamination level less than 1 ppm. The method includes exciting the optical fluoride crystal with the fluorescence spectrometer selectable wavelength incident radiation and detecting excited luminescence light from the optical flu crystal impurity to provide a contaminant level less than 50 ppb.

The invention includes a method of making a below 200 nm wavelength optical lithography element. The method includes providing a below 200 nm wavelength transmitting optical fluoride crystal and a fluorescence spectrometer for producing a selectable wavelength incident radiation and detecting excited luminescence light produced by the incident radiation. The method includes exciting the optical fluoride crystal with the fluorescence spectrometer selectable wavelength incident radiation and detecting excited luminescence light from the optical fluoride crystal impurity to provide a contaminant level measurement less than 50 ppb and forming the optical fluoride crystal into a below 200 nm wavelength optical element having a less than 50 ppb measurement contaminant level.

The invention includes a method of making a below 200 nm wavelength transmitting optical fluoride crystal. The method includes providing a premelt calcium fluoride crystal solid. The method includes melting the premelt calcium fluoride crystal solid to form a calcium fluoride melt and growing a calcium fluoride crystal from the melt to provide an optical calcium fluoride crystal for transmitting below 200 nm wavelengths. The method includes providing a fluorescence spectrometer having a light source for producing a 200 to 210 nm selectable wavelength incident radiation and a detector for detecting excited luminescence light in the wavelength range of 210–260 nm produced by the incident radiation and measuring a lead contaminant level in calcium fluoride with said fluorescence spectrometer.

The invention includes a below 200 nm wavelength transmitting optical fluoride crystal of calcium fluoride having a below 200 nm transmission greater than 99%/cm and a lead ppb excitation level less than 20.

BRIEF DESCRIPTION OF THE DRAWINGS

FIG. 1B shows an embodiment of the invention.

DETAILED DESCRIPTION OF THE PREFERRED EMBODIMENTS

Figure 1A:
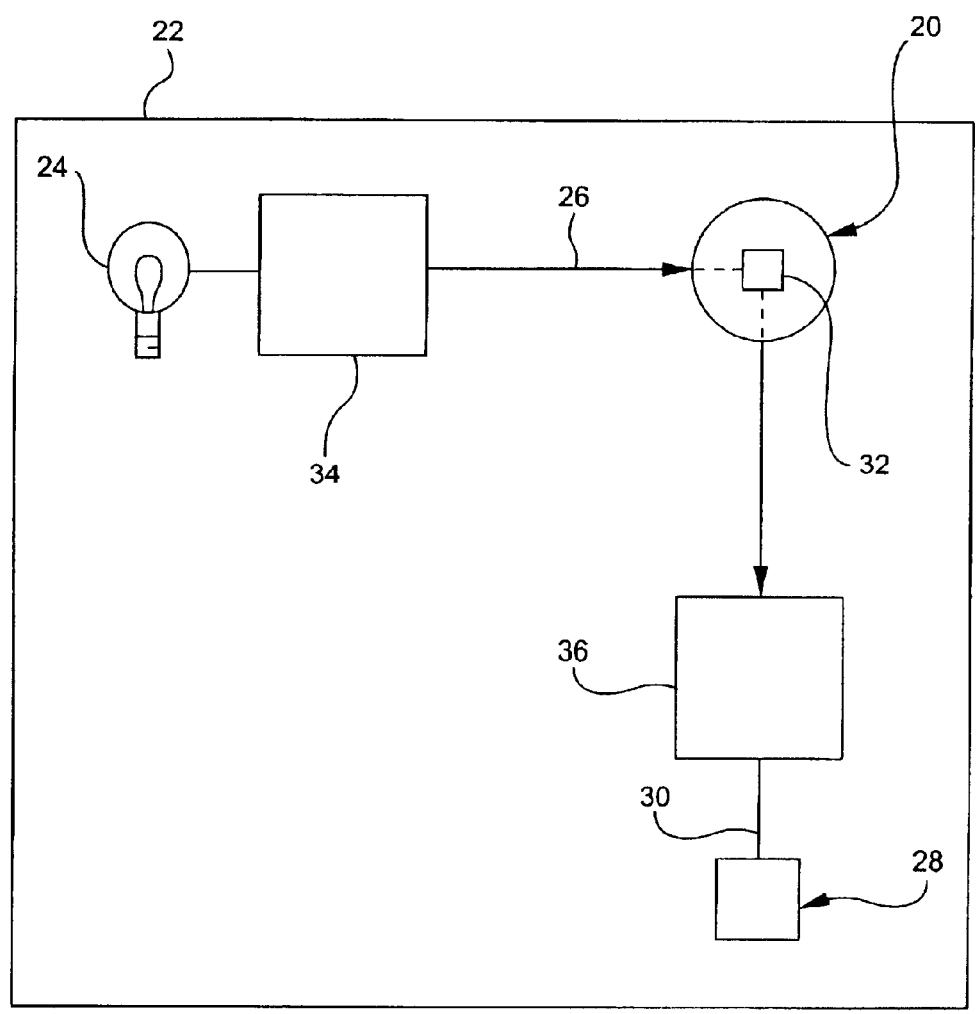
FIG. 1A shows an embodiment of the invention.
Figure 2:
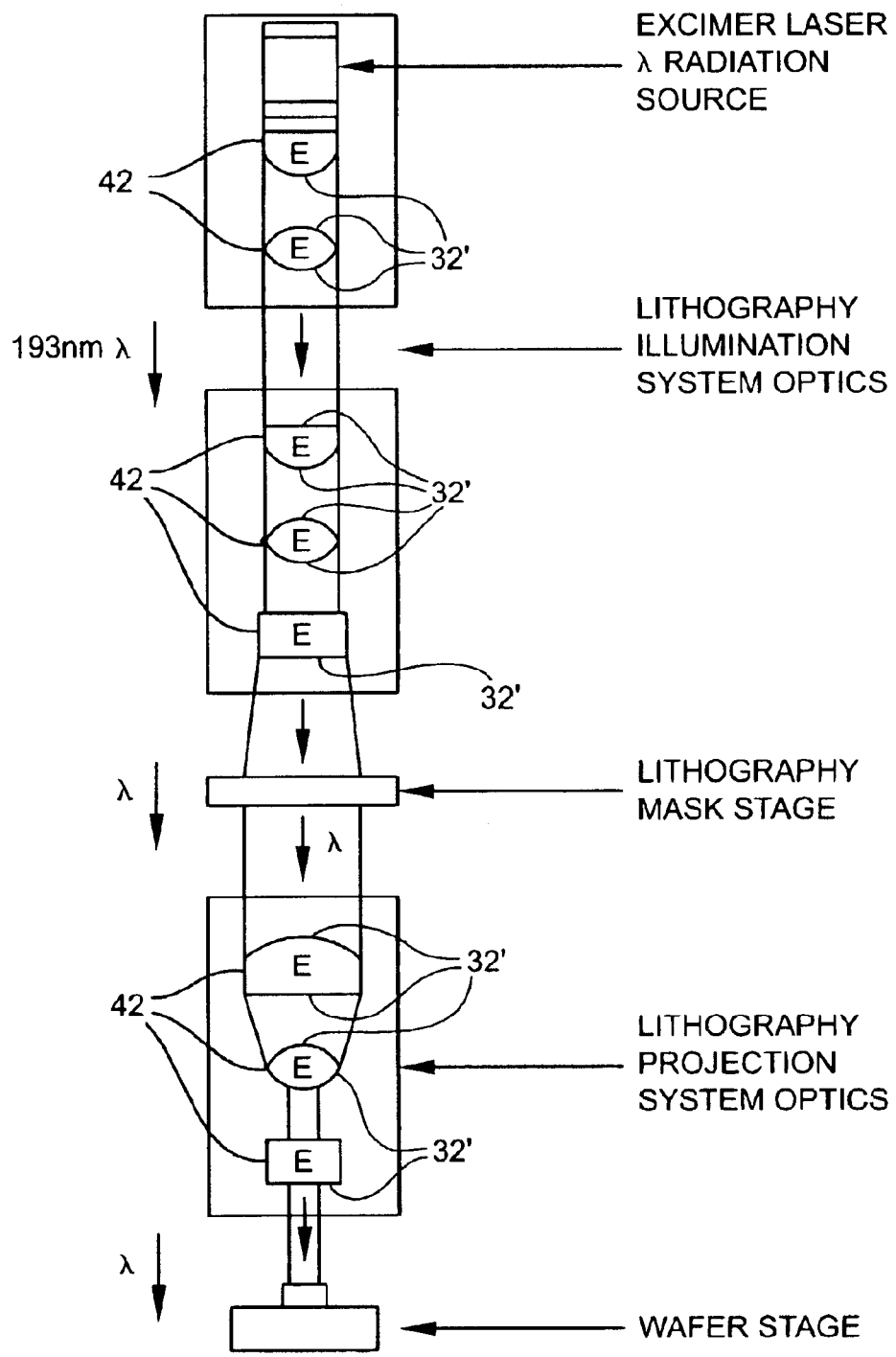
FIG. 2 shows an embodiment of the invention.
Figure 3:
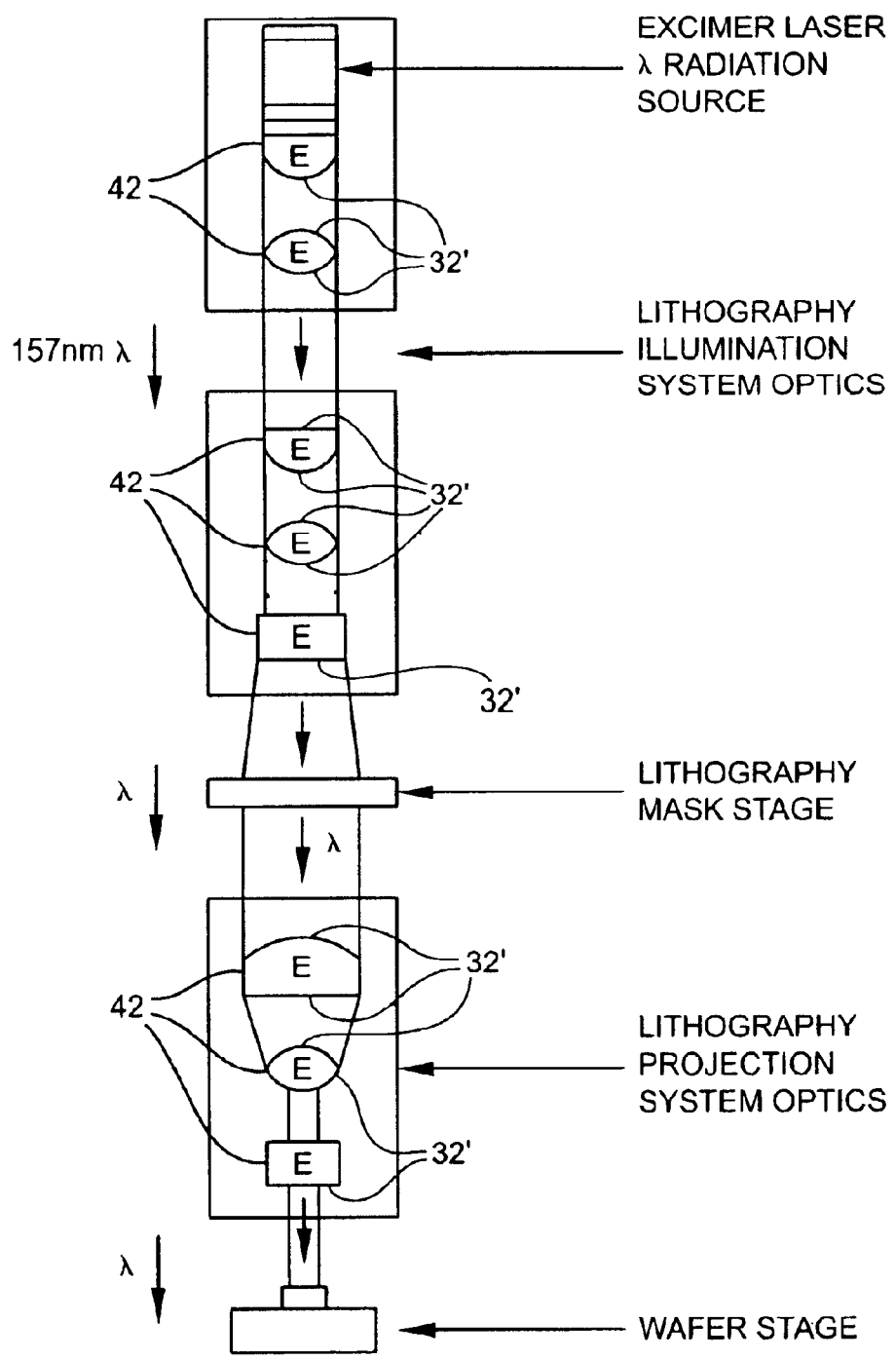
FIG. 3 shows an embodiment of the invention.

The invention includes a method of detecting sub-ppm lead impurity levels in a below 200 nm transmitting optical calcium fluoride crystal. The method includes providing a below 200 nm wavelength transmitting optical calcium fluoride crystal 20. Optical calcium fluoride crystal 20 preferably is an optical fluoride crystal with a lead contaminant level less than 1 ppm. The method includes providing a fluorescence spectrometer 22 having a light source 24 for producing a 200 to 210 nm selectable wavelength incident radiation 26 and a detector 28 for detecting excited luminescence light 30 in the wavelength range of 210–260 nm produced by the incident radiation. The method includes exciting a first luminescence area 32 of crystal 20 with the 200–210 nm selectable wavelength incident radiation 26 and detecting with detector 28 excited 210–260 luminescence light 30 produced from the crystal luminescence area 32 of crystal 20 by the 200–210 nm selectable wavelength incident radiation to provide a lead ppb impurity level measurement less than 100 ppb, preferably less the 50 ppb. Preferably light source 24 is a broad band wavelength light source such as a lamp. Preferably lamp 24 is a broad band noncoherent light source compared to a laser light source. Providing a 200 to 210 nm selectable wavelength incident radiation 26 preferably includes utilizing an excitation wavelength selector 34 such as an excitation monochromator/filter to controllably select the wavelengths in the 200–210 range. Detecting excited 210–260 nm luminescence light 30 preferably includes utilizing an emission wavelength selector 36 such as an emission monochromator/filter grating to controllably select the wavelength to be detected within the 210–260 nm range. The incident radiation wavelength is selected and scanned from 200–210 nm and the excited luminescence light is detected and measured to provide a lead ppb impurity level measurement less than 20 ppb by weight. Preferably the excited 210–260 nm luminescence light detected provides a lead impurity level less than 10 ppb, more preferably <1 ppb, more preferably <0.1 ppb, and most preferably <0.01 ppb by weight for the crystal luminescence area. The method preferably includes exciting a second luminescence area 38 of crystal 20 to provide a second lead ppb impurity level measurement. The second luminescence area is different and separate from the first luminescence area. The method provides for real time determination of lead impurity levels throughout the crystal, with such lead impurity levels also being of varying amounts. The method preferably includes exciting a plurality of luminescence areas of the crystal to provide a lead impurity level mapping of the crystal, with such measurement mapping providing average lead content and peak lead content and location of lead impurity concentrations. As shown in FIG. 1B, in an embodiment of the invention, a fluorescence spectrometer including optical waveguide fiber 40 is utilized to transmit the incident radiation and excited luminescence light at multiple locations (such as of first and second luminescence areas 32 and 38) to real-time map the lead impurity levels of the crystal with a plurality of luminescence measurements.

The invention includes a method of measuring below 1 ppm impurity levels in an optical fluoride lithography crystal for transmitting below 200 nm wavelength light. The method includes providing a fluorescence spectrometer 22 for producing a selectable wavelength incident radiation 26 with a wavelength greater than 200 nm, preferably in the range of 200 to 210. The provided fluorescence spectrometer is also for detecting excited luminescence light 30 produced by the greater than 200 nm incident radiation 26. The method includes providing an optical fluoride crystal 20 for transmitting below 200 nm wavelength of light with the crystal containing an impurity at a contamination level less than 1 ppm. Preferably the impurity contained in the crystal at the <1 ppm contamination level is lead. The method includes exciting optical fluoride crystal 20 with the fluorescence spectrometer selectable wavelength incident radiation 26 and detecting excited luminescence light 30 from the optical fluoride crystal impurity to provide a contaminant level measurement less than 50 ppb, preferably less than 20 ppb. Preferably exciting the crystal and detecting the excited luminescence light provides a contaminant level measurement less than 100 ppb, more preferably less than 1 ppb, and most preferably less than 0.1 ppb, and <0.01 ppb. In a preferred embodiment, the optical fluoride crystal contains a lead impurity at a contamination level less than 1 ppm and detecting excited luminescence light from the crystal's lead impurity provides a lead contaminant level measurement <50 ppb, preferably <10 ppb lead, <0.1 ppb lead, more preferably <0.01 ppb lead. Preferably the lead impurity is excited in the fluoride crystal with 200 to 210 nm selectable wavelengths, preferably with the detected excited luminescence light being in the range of 210–260 nm. Preferably the fluoride crystal having a measured lead impurity level <50 ppb is comprised of calcium, most preferably CaF2 with a 157 nm transmission ≧99%/cm. Preferably the method provides a contaminant level measurement with a detection limit less than 10 ppb, more preferred <1 ppb, and more preferred <0.1 ppb. In an embodiment the provided fluorescence spectrometer has an optical waveguide 40, preferably a remote fiber optic spectrometer accessory attachment, and exciting the crystal 20 includes transmitting incident radiation 26 through the optical waveguide 40 to the crystal and detecting includes transmitting the excited luminescence light 30 from the crystal through the optical waveguide to detector 28. Preferably the method includes mapping a variation of the contaminant level in the fluoride crystal by exciting and detecting excited luminescence light at a plurality of different surface locations of the crystal. Preferably the fluorescence spectrometer is calibrated with an optical fluoride crystal reference having a known contaminant level, preferably a known lead contaminant level, most preferably in a calcium fluoride crystal. Preferably the method includes measuring at least one luminescence intensity of the crystal. Comparative luminescence measurements for lead contaminant level evaluation in calcium fluoride crystals preferably utilize direct measurement of luminescence intensity, and preferably not corrected spectra-modes.

Figure 4:
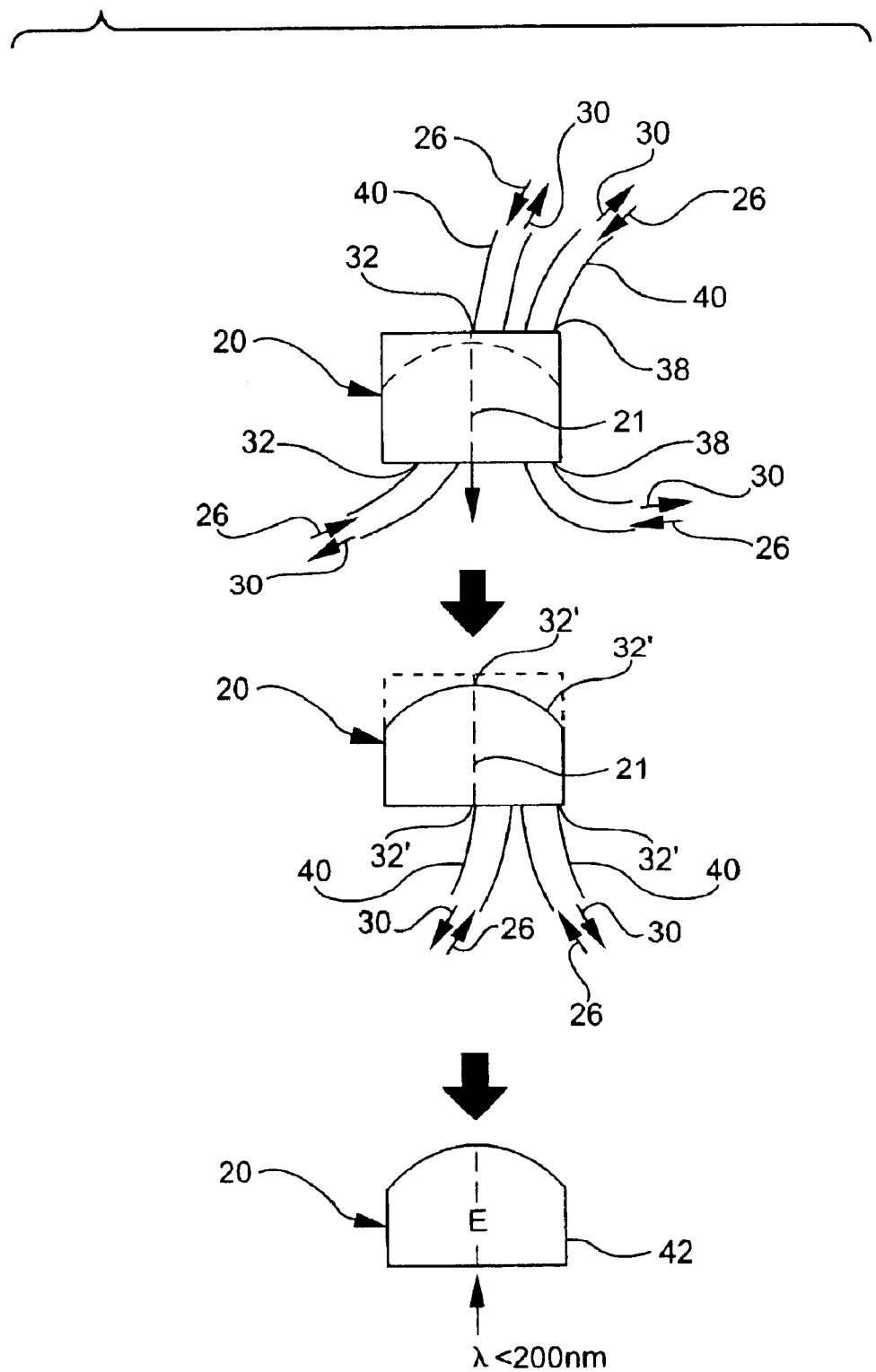
FIG. 4 shows an embodiment of the invention.

The invention includes a method of making a below 200 nm wavelength optical element E for transmitting below 200 nm wavelength light such as F2 excimer laser 157 nm output or an ArF excimer laser 193 nm output. Preferably the method includes making a λ<200 nm optical lithography element 42 of high optical quality from an optical fluoride crystal 20 having a fluorescence spectrometer contaminant level measurement <50 ppb, preferably <20 ppb. The method includes providing a below 200 nm wavelength transmitting optical fluoride crystal 20 and providing a fluorescence spectrometer 22 for producing a selectable wavelength incident radiation 26 and detecting excited luminescence light 30 produced by the incident radiation 26. The method includes exciting optical fluoride crystal 20 with the fluorescence spectrometer selectable wavelength incident radiation 26 and detecting excited luminescence light 30 from the crystal to provide a contaminant level measurement less than 50 ppb and forming the optical fluoride crystal 20 into a below 200 nm wavelength optical element E having a less than 50 ppb measured contaminant level. In a preferred embodiment, such as shown in FIG. 4, a spectrometer waveguide 40 is utilized to transmit incident radiation 26 and excited luminescence light 30 and to measure multiply luminescence areas 32, 38 and 32 and to map variations of contaminant level of crystal 20 and optical element 42 formed therefrom. Preferably crystal 20 and optical element 42 have a measured contaminant level less than 10 ppb, more preferably <1 ppb, more preferably <0.1 ppb, and most preferred <0.01 by weight. Providing below 200 nm transmitting optical fluoride crystal 20 preferably includes providing a calcium fluoride crystal with a λ<200 nm transmission greater than 99%/cm and exciting the calcium fluoride crystal 20 includes exciting with the fluorescence spectrometer selectable wavelength incident radiation in the range of 200 to 210 nm and detecting excited luminescence light in the wavelength range of 210–260 nm to provide a lead contaminant level measurement less than 50 ppb, preferably a lead contaminant level measurement <20 ppb, more preferably <10 ppb, more preferably <1 ppb, more preferably <0.1 ppb and most preferably <0.01 ppb by weight. The method provides an optical lithography element 42 with a measured contaminant level less than 50 ppb, measured at a luminescence area 32 and if optical coatings are to be applied to the crystal surface, preferably the luminescence area 32 is measured prior to any such coating.

Figure 5:
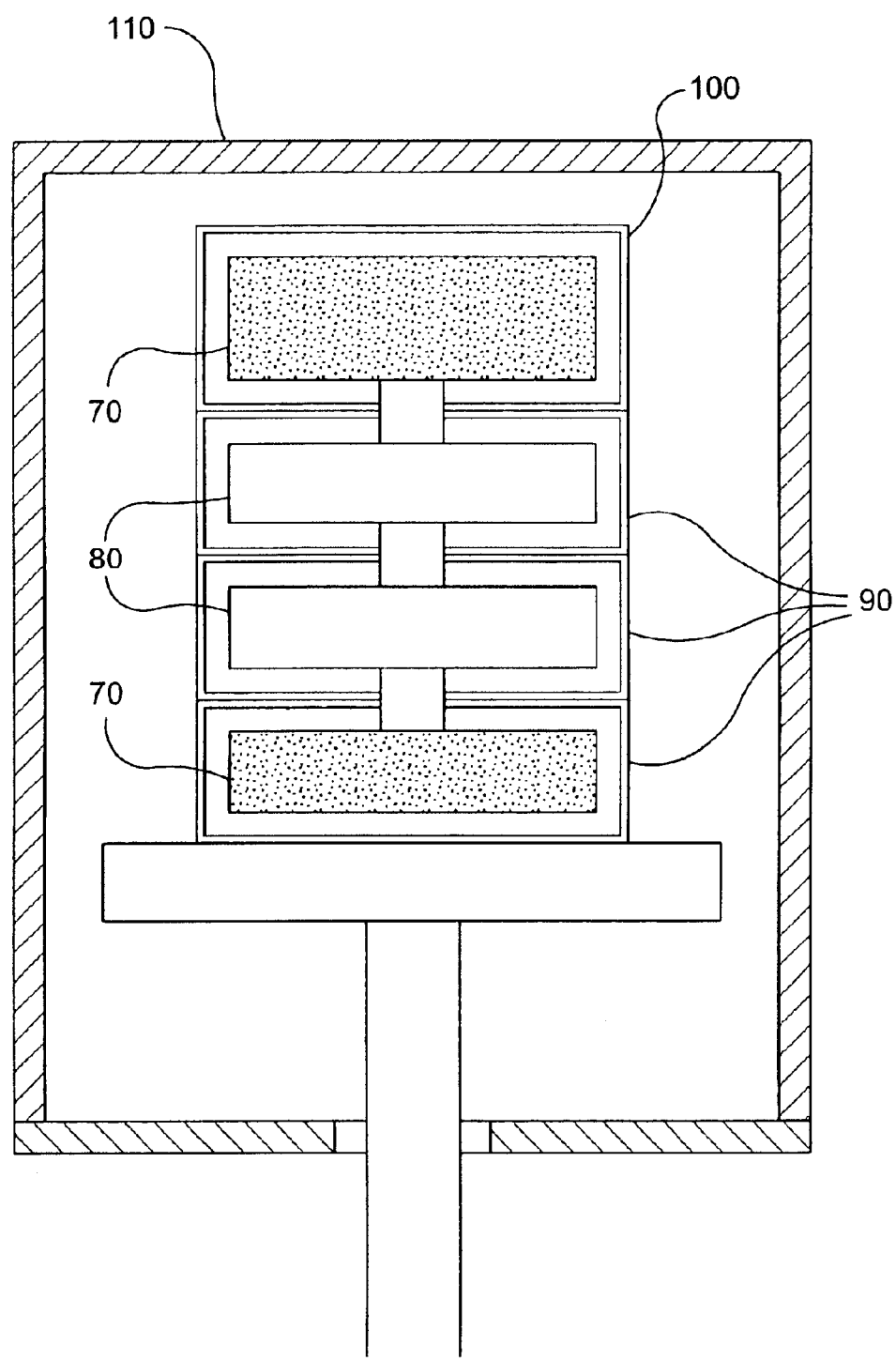
FIG. 5 shows an embodiment of the invention.
Figure 6:
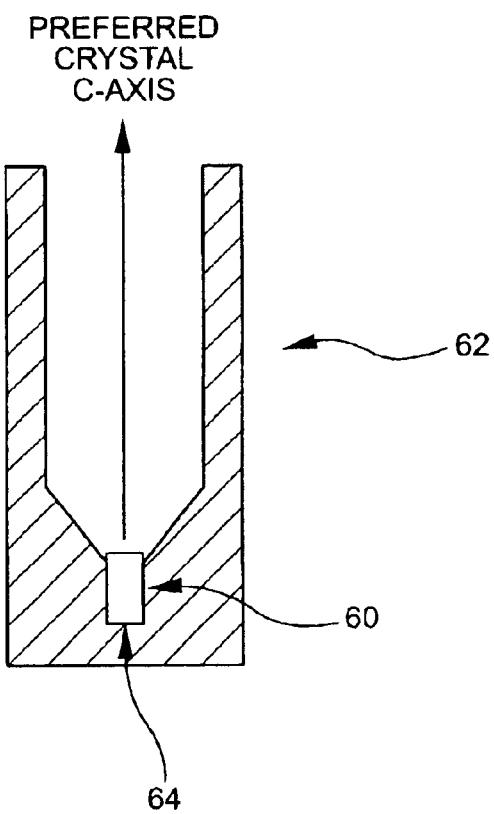
FIG. 6 shows an embodiment of the invention.
Figure 7:
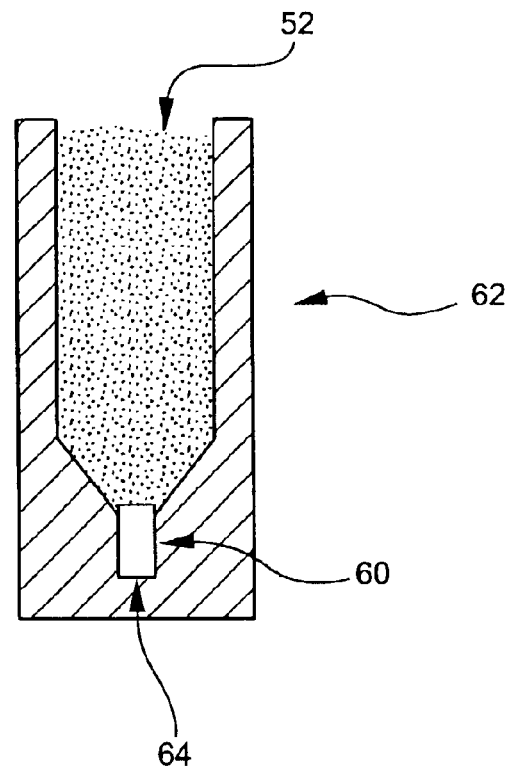
FIG. 7 shows an embodiment of the invention.
Figure 8:
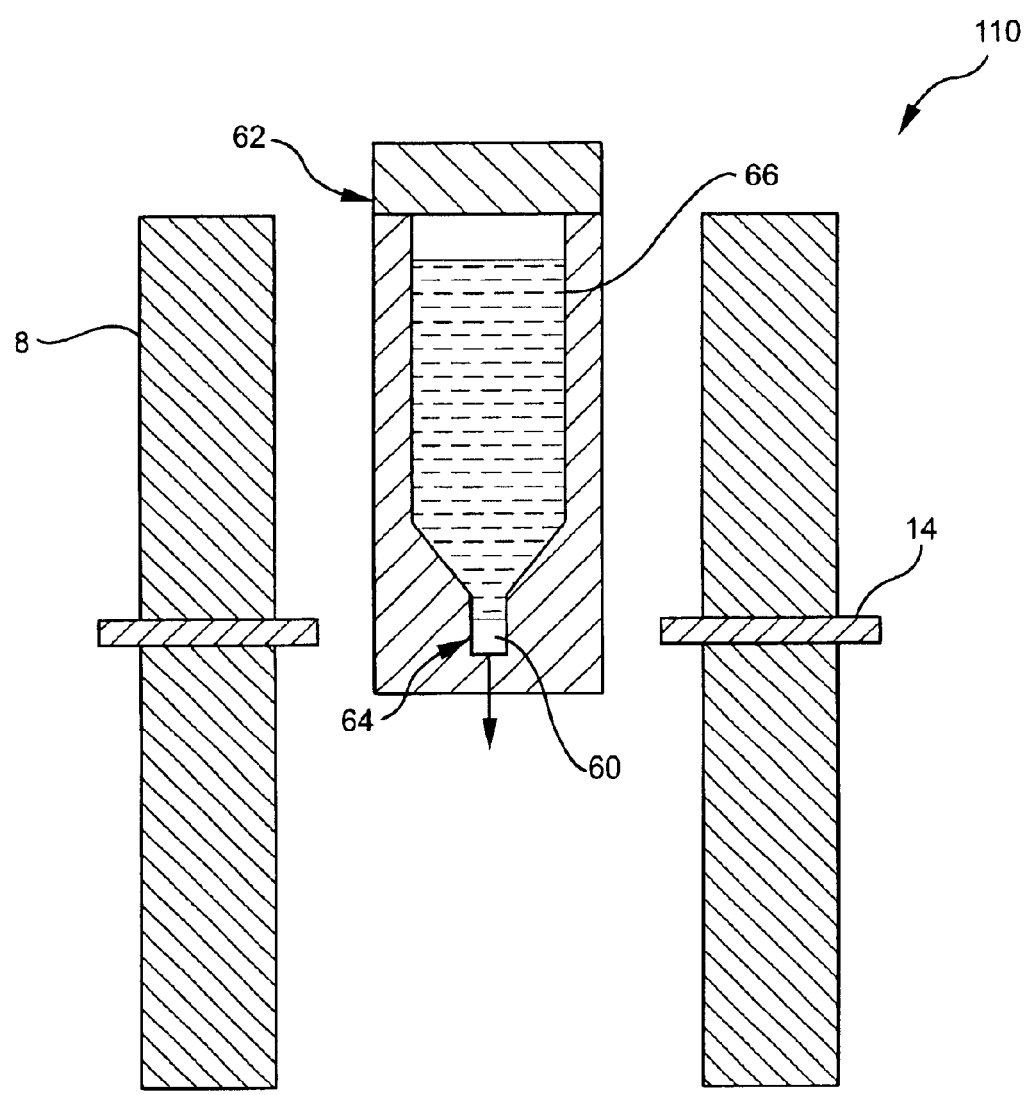
FIG. 8 shows an embodiment of the invention.
Figure 9:
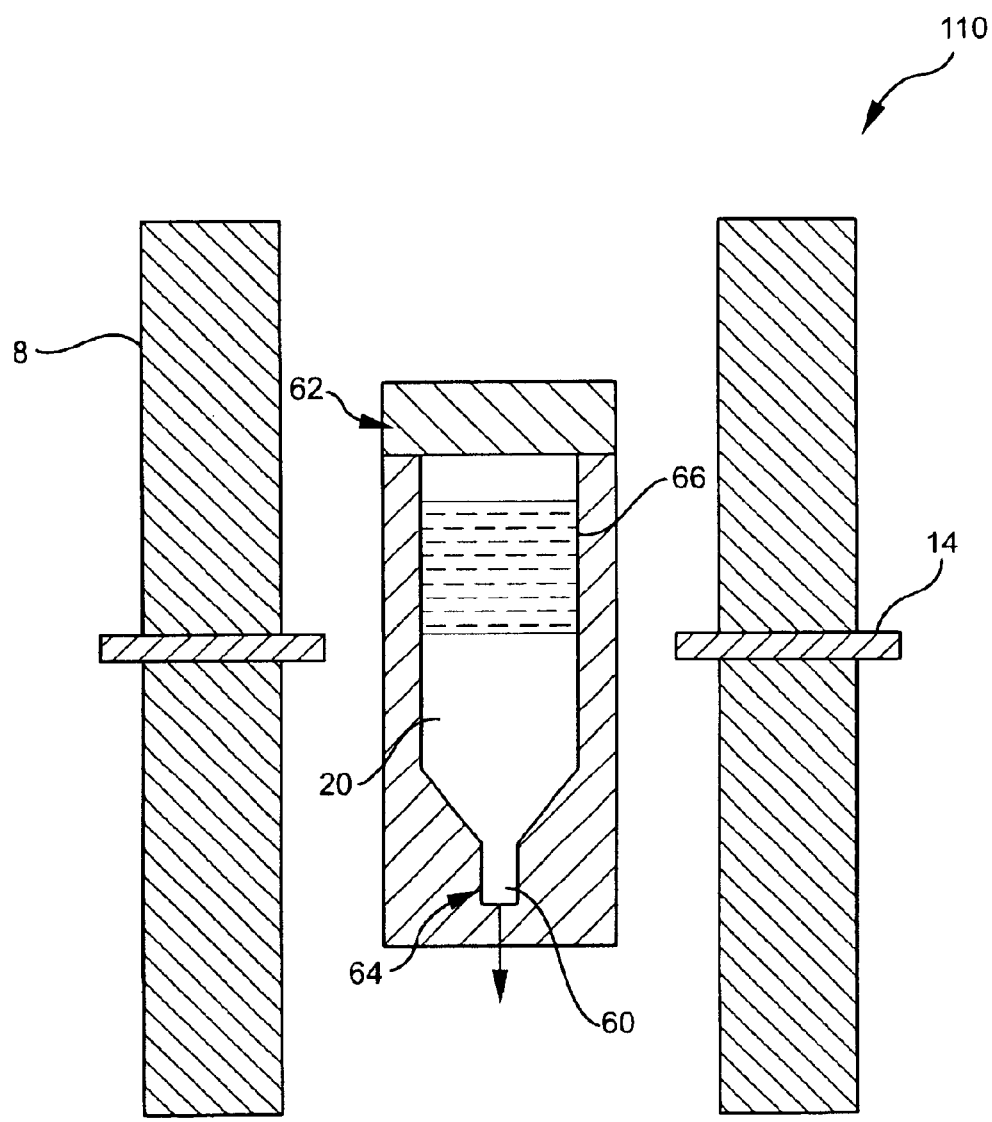
FIG. 9 shows an embodiment of the invention.
Figure 10:
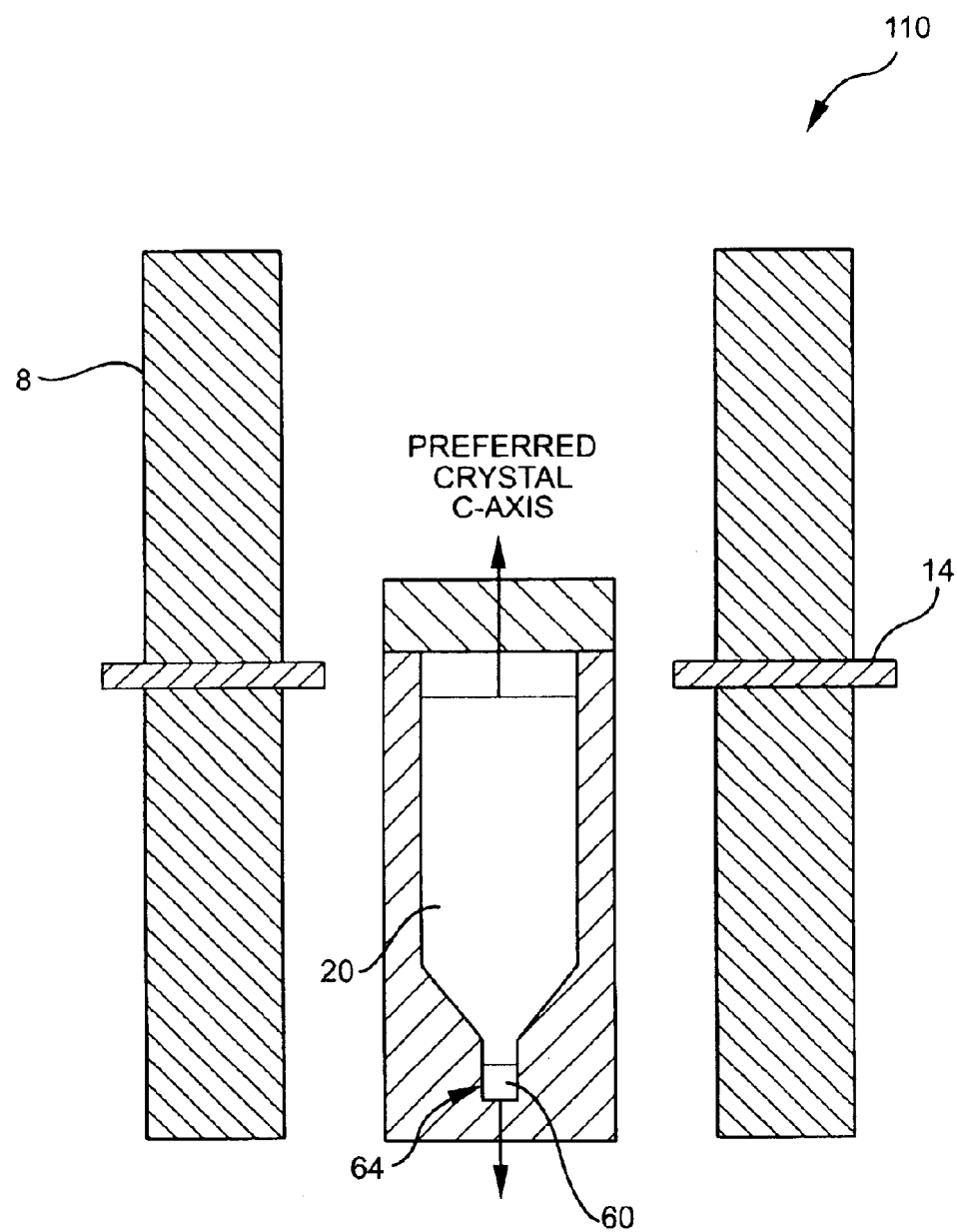
FIG. 10 shows an embodiment of the invention.

The invention includes a method of making a below 200 nm wavelength transmitting optical fluoride crystal 20. The method includes providing a premelt calcium fluoride crystal solid and melting the calcium fluoride crystal solid to form a calcium fluoride melt and growing a calcium fluoride crystal from the melt to provide an optical calcium fluoride crystal for transmitting below 200 nm wavelengths. The method includes providing a fluorescence spectrometer having a light source for producing a 200 to 210 nm selectable wavelength incident radiation and a detector for detecting excited luminescence light in the wavelength range of 210–260 nm produced by the incident radiation and measuring a lead contaminant level in the calcium fluoride with the fluorescence spectrometer. In an embodiment, measuring the lead contaminant level in the calcium fluoride with the fluorescence spectrometer includes measuring the lead contaminant level in the premelt calcium fluoride crystal solid. In an embodiment measuring the lead contaminant level in the calcium fluoride with the fluorescence spectrometer includes measuring the lead contaminant level in the calcium fluoride crystal grown from the calcium fluoride melt. In an embodiment, the lead contaminant level in the calcium fluoride is measured with the fluorescence spectrometer when the crystal is in the formed shape of an optical element E before optical coating. In an embodiment, the lead contaminant level in the calcium fluoride is measured when the premelt calcium fluoride crystal solid is in the particulate form. In an embodiment, the lead contaminant level in the calcium fluoride is measured prior to crushing into the particulate form and/or during the crushing process of crushing from a solid block into particulate powder. Preferably the measuring and monitoring of lead contaminant level in the crystal making process provides a grown optical calcium fluoride crystal for transmitting below 200 nm wavelengths with a lead ppb contaminant excitation level less than 50 ppb, more preferably <20 ppb. Preferably the grown crystal 20 has a lead ppb contaminant excitation level less than 10 ppb, preferably <1 ppb, more preferably <0.1 ppb, and most preferably <0.01 ppb. FIG. 5 shows an embodiment of the invention wherein a vacuum controlled atmosphere crystallization furnace 110 is loaded with stacked interconnected graphite crucibles 90 and top reservoir crucible 100. The middle crucibles are loaded with premelt calcium fluoride crystal solid dense discs 80. Premelt calcium fluoride crystal solid discs 80 are purified and densified CaF2 preferably obtained from a premelt process wherein high purity raw material is purified and densified by heating and melting with a fluorinating agent. In an embodiment the premelt calcium fluoride crystal solid is obtained by premelt purification and densification utilizing PbF2 as a fluorinating agent with the calcium fluoride, with the controlled atmosphere vacuum furnace operated to remove volatile lead and oxygen products from the crystal material. In an embodiment, such as shown in FIG. 5, the furnace can also be loaded with calcium fluoride powder particulate 70 which can include a fluorinating agent such as lead fluoride. The premelt calcium fluoride crystal solid loaded into crystal growth furnace 100 is melted in the crucibles 90 and 100 into a calcium fluoride melt which is then grown into a calcium fluoride crystal 20 by slowly cooling the melt within the crystal growth furnace, such as lowering through the thermal gradient in a Stockbarger crystal growth process. In another embodiment of the invention shown in FIGS. 6–10, a growth crucible 62 having a preferred crystal axis oriented seed crystal 60 in a seed crystal receiver 64 is utilized.

Figure 11:
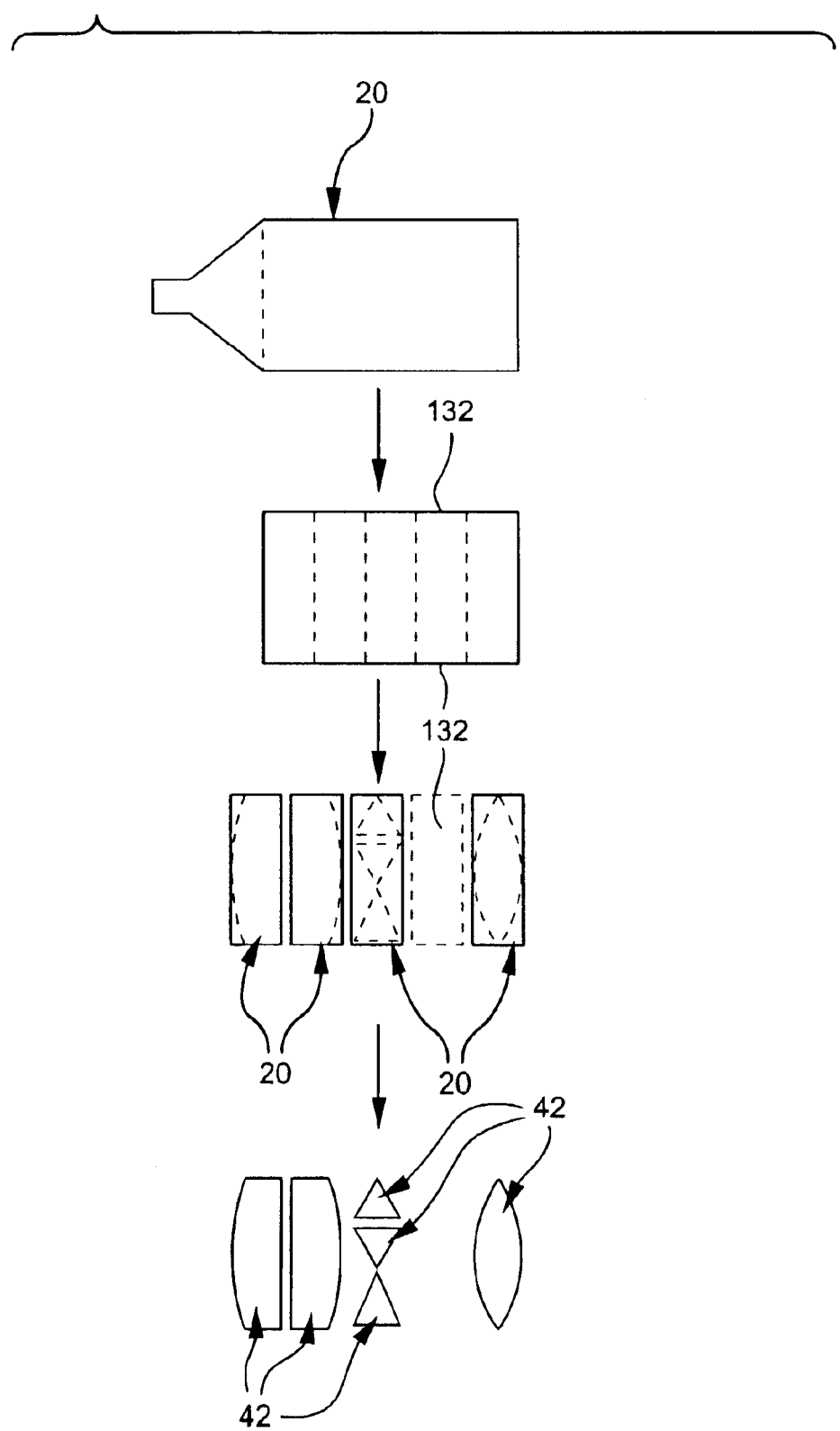
FIG. 11 shows an embodiment of the invention.
Figure 12:
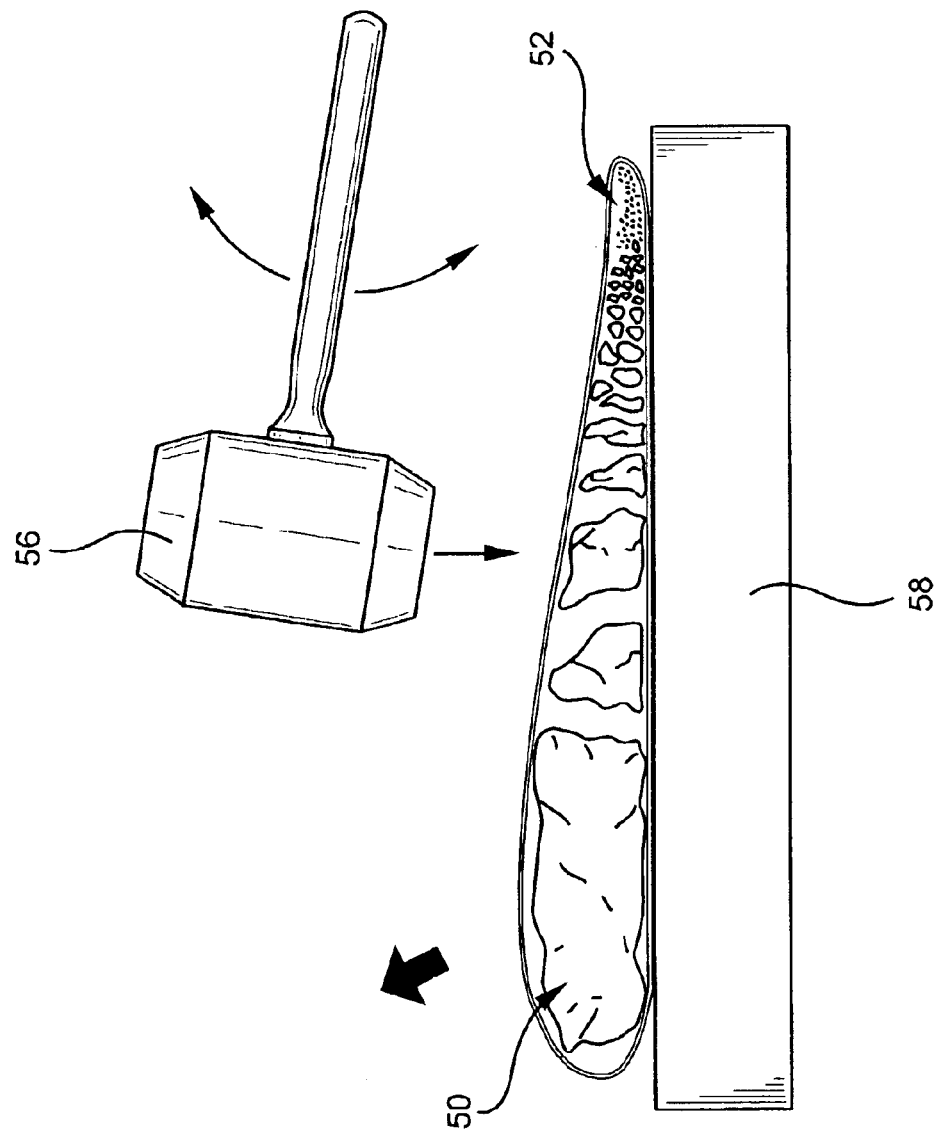
FIG. 12 shows an embodiment of the invention.
Figure 13A:
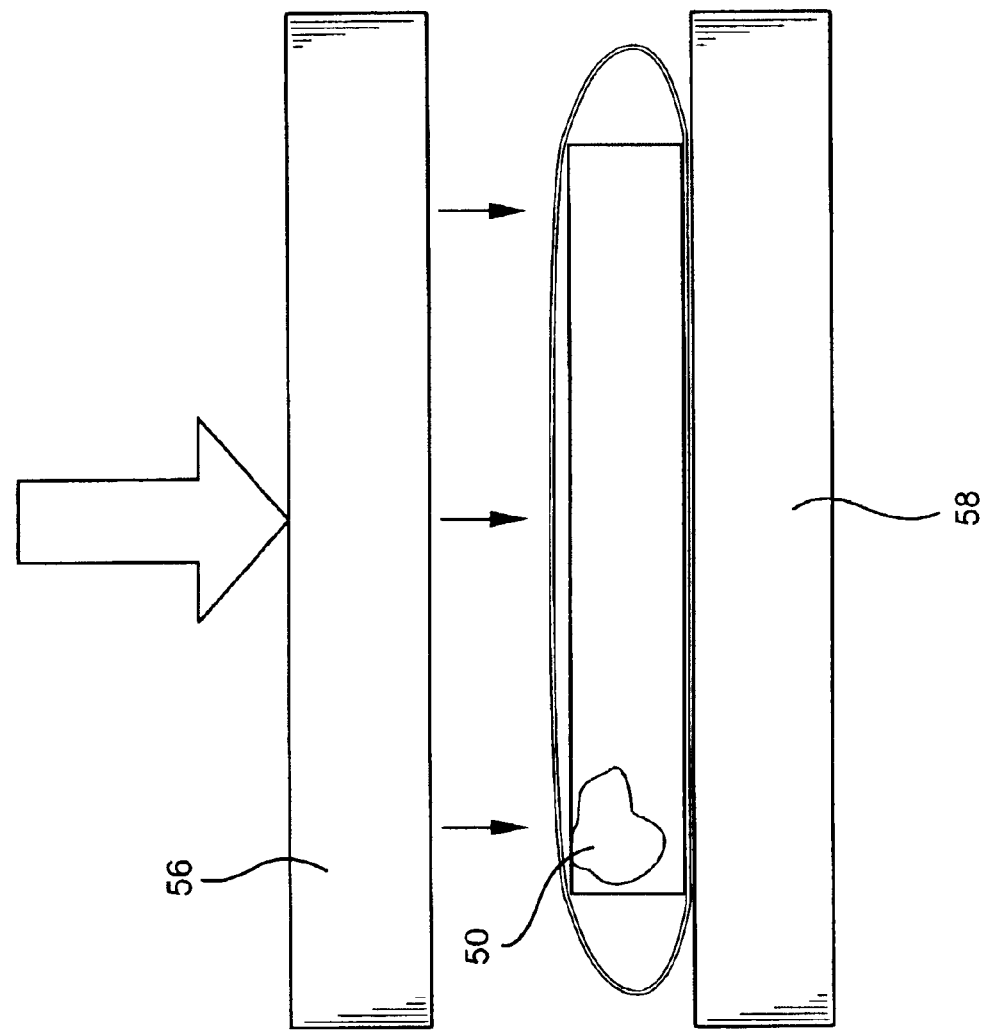
FIGS. 13a–c shows an embodiment of the invention.
Figure 13B:
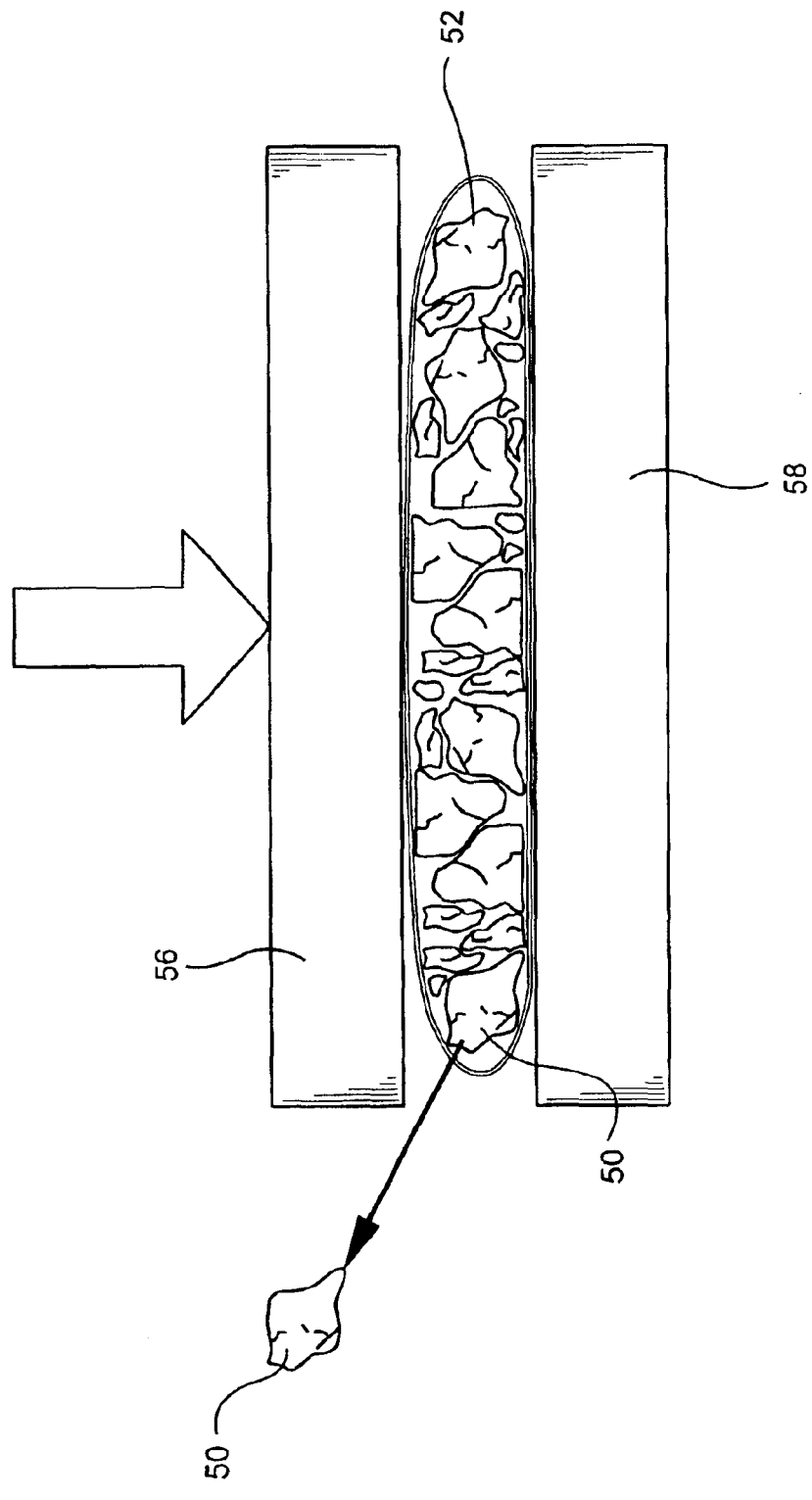
Figure 13C:
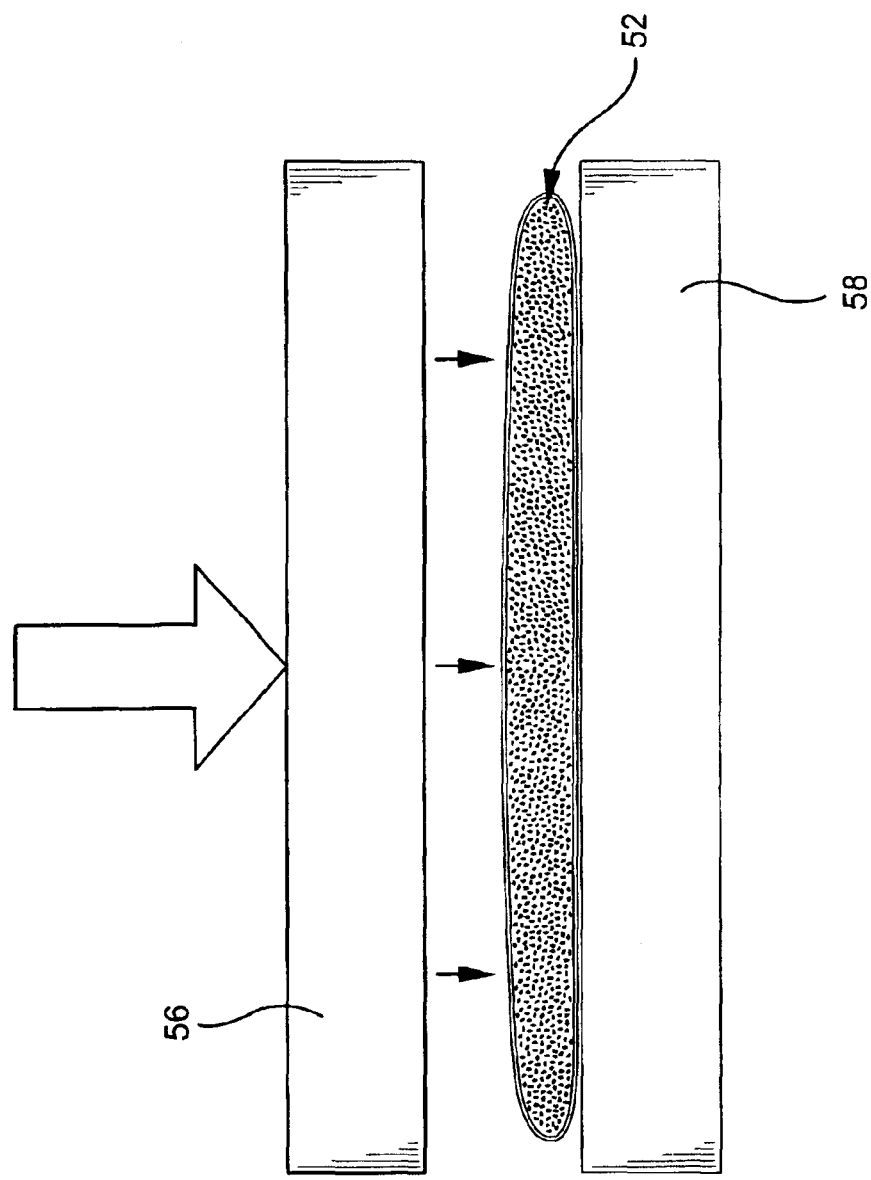

Premelt calcium fluoride crystal solid particulate 52 is loaded into crucible 62. The crystal growth crucible containing the premelt calcium fluoride crystal solid is loaded into an optical fluoride growth furnace 110, which includes a high temperature upper melt zone 8 and a thermal baffle 14 which provides a thermal gradient for crystal growth solidification. The calcium fluoride crystal solid loaded into crucible 62 is melted in the high temperature zone 8 of furnace 100 to form a calcium fluoride melt 66. Calcium fluoride optical crystal 20 is grown from the melt 66 by lowering through the crystal growth solidification zone of baffle 14 to provide optical fluoride crystal 20 for transmitting below 200 nm wavelengths. The method includes making the crystal 20 by utilizing a fluorescence spectrometer 22 to produce 200 to 210 nm selectable wavelength incident radiation and detect excited luminescence light in the 210–260 nm range to measure lead contaminant levels in calcium fluoride such as in the premelt calcium fluoride crystal solids 80 and 52, in the grown crystal 20, and the seed 60. The spectrometer 22 is preferably utilized throughout the crystal manufacturing process to measure, monitor, and control the calcium fluoride lead content, particularly when lead fluoride is used as a fluorinating agent, which needs to be removed from the end product crystal 20 and optical element E thereof to provide high transmission and optical properties at below 200 nm wavelengths. The spectrometer calcium fluoride lead contaminant level measurements are utilized to provide measurements below 50 ppb, preferably below 20, preferably below 10 ppb, more preferably below 1 ppb, <0.1 ppb, and most preferably <0.01 ppb by weight. The spectrometer calcium fluoride lead contaminant level measurements can be utilized to map variation of lead contaminants in the calcium fluoride crystal and identify high lead contaminant level areas of crystals and remove them from the optical fluoride crystal optical element making process as rejects. Such as shown in FIG. 11, the measurements can be utilized to identify a high contaminant local crystal region luminescence area 132, and remove such high contaminant region luminescence area 132 from further processing into separate optical element blank preform crystals 20 and into optical elements 42 made therefrom. Such as shown in FIGS. 12–13C the measurements can be utilized to identify a high contaminant local crystal luminescence area 50 in premelt solid 52 to provide a high purity premelt solid particulate resulting from a crushing process using crushers 56 and 58. The high contaminant luminescence areas 50 can be identified with a fluorescence spectrometer and be removed during the crushing process from the low contaminant luminescence areas to result in the production of a separated low impurity premelt solid 52.

Such a method of making optical fluoride crystals and optical elements therefrom while monitoring and measuring impurity levels, particularly lead contaminants, utilizing a fluorescence spectrometer provides for a high quality crystal with excellent optical properties including high below 200 nm transmission greater than 99%/cm, most preferably 157 nm transmission greater than 99%/cm. The method of making optical fluoride crystals produces fluoride crystals with a lead excitation level less than 50 ppb, more preferably <20 ppb, more preferably <10 ppb, more preferably <1 ppb, more preferably <0.1 ppb, and most preferably below 200 nm wavelength transmitting calcium fluoride elements with a lead ppb excitation level less than 0.01 ppb by weight. The invention includes a below 200 nm wavelength transmitting optical fluoride crystal. The optical fluoride crystal 20 is comprised of calcium fluoride having a below 200 nm transmission greater than 99%/cm, preferably 157 nm transmission >99%/cm, and a lead ppb excitation level less than 20 by fluorescence spectrometer excitation measurement with 200 to 210 nm incident radiation and detection of 210–260 nm excitation light. Preferably the lead ppb excitation level is less than 10, more preferably <1, more preferably <0.1 most preferably <0.01 ppb by weight. Preferably the calcium fluoride crystal 20 has an average lead ppb excitation level less than 10 and a peak lead ppb excitation level less than 20 by surface area luminescence measurement. Preferably, the average lead ppb is less than 5 and the peak is less than 10 ppb. Preferably the average is less than 0.1 ppb and the peak is less than 1 ppb. The luminescence analysis method of the invention can be utilized throughout the optical fluoride crystal optical element manufacturing process from the feedstock raw material stage and the end product optical element.

EXAMPLES

The invention will be further clarified by the following examples.

In practicing the invention a fluorescence spectrometer 22, such as a Perkin-Elmer LS-50B spectrofluorimeter (Perkin-Elmer Analytical Instruments, 710 Bridgeport Avenue Shelton, Conn. 06484-4794 U.S.A., Phone: 203-925-4600, 800-762-4000, (+1) 203-762-4000) is utilized. In a preferred embodiment the light source 24 is comprised of a xenon arc lamp. Preferably the invention provides for comparative luminescence measurements of Pb contamination levels utilizing direct measurements of fluorescence intensity as compared with a corrected spectra mode. In an embodiment the invention utilizes a waveguide 40 flexible fiber probe attachment connected to the fluorescence spectrometer 22. Preferably the invention provides for nondestructively testing with minimal preparation with no surface preparation/polishing needed. In an embodiment the invention includes removing a small crystal sample ((small measurement size sample piece-1×1×0.5 cm, or 2×2×0.5 cm) with polished faces and one side at least) from a larger crystal ingot body. A small measurement size sample piece is cut and polished and inserted into the fluorescence spectrometer for measurement therein. The use of a fiber waveguide attachment 40 allows for quantifying Pb content in the about 1 cm thick surface layer thickness of a large crystal body located outside of the spectrofluorimeter without the need for cutting and polishing. Mapping of a crystal can be done with crystal surface grid resolution of less than 2 cm2, such as with individual measurements of about 1 cm2. Preferably, very low levels of impurities can be measured by utilizing a high sensitivity order of a spectrometer grating as a filter with detecting the impurity luminescence wavelengths, such as by using a higher grating diffraction order like the second diffraction order of the detector grating for the improved sensitivity of Pb luminescence wavelengths for low Pb ppb levels like 0.01. Preferably the quantitative luminescence analysis of the impurity in the optical fluoride crystal is based on comparison of the luminescence intensity of the tested sample with the luminescence intensity of reference samples of known impurity content. Both measurements (tested and reference samples) should be performed with the use of the same measurement set-up under the same conditions. The invention provides for calcium fluoride crystals with well below 100 ppb lead concentrations, preferably below 1 ppb based on lead luminescence. Preferably the invention provides a below 200 nm wavelength transmitting optical fluoride crystal of calcium fluoride having a below 200 nm transmission greater than 99%/cm at 157 nm, a Na by weight impurity level less than 0.5 ppm, a K by weight impurity level less than 0.5 ppm, and a lead ppb excitation level less than 10 by fluorescence spectrometer excitation measurement with 200 to 210 incident radiation and detecting 210–260 nm excitation light.

This invention provides for controlling crystal quality of fluoride crystals for use in applications at wavelength <200 nm by measuring lead impurity luminescence in the wavelength range 210–260 nm under excitation in the range between 200 and 210 nm.

Fluoride crystals exhibit excellent properties as optical materials for application at wavelength <200 nm because of their high transmission characteristics. But this is true only for crystals free of oxygen impurity. Specifically, the transmission of fluoride crystals at wavelengths 193 and 157 nm (radiation of ArF and F2 lasers correspondingly) can be sufficiently reduced when oxygen species are present in crystals.

In order to obtain fluoride crystal with excellent transmission characteristics it is preferred to add scavengers to remove oxygen species from the crystal raw material, such as a lead fluoride scavenger. A lead fluoride scavenger can effectively remove O, but lead element Pb can remain in the crystal after scavenging. Lead impurity has an adverse influence on the crystal transmission characteristics at wavelengths <200 nm. In particular, transmission at 157 nm degrades drastically when lead impurity is present in a crystal.

Qualification of manufactured crystals by measuring the internal transmission at 193 and 157 nm is a complicated procedure requiring a moisture-free spectrometer by applying purging or vacuum and special cleaning of sample surfaces. Such procedures raise the cost of crystal manufacturing. We have proposed to control fluoride crystals in respect of their transmission at wavelengths below 200 nm by measuring Pb absorption above 200 nm, preferably between 200 and 210 nm in Corning Incorporated French Patent Application No. 01 16097 filed Dec. 13, 2001 (Method of Testing a Fluoride Crystal for Purity Relative to Lead by M. Pell, A. Mayolet, N. Timofeev), which is hereby incorporated by reference. The Pb detection limit provided by this method was shown to be 1 ppb when sample path length was not less than 100 mm.

We propose to use our present luminescence technique for evaluating Pb impurity content in fluoride crystals, and thus to make qualification of grown crystals in respect of their transmission at wavelengths below 200 nm, based on the relationship between Pb content and transmission at wavelengths below 200 nm. Compared to absorption technique, the present method allows: (i) to decrease Pb detection limit up to 0.1 ppb; (ii) to perform Pb analysis locally in different points of crystal ingot volume, because samples size needed for luminescence measurements can be small enough (for example 10×10×5 mm).

Fluoride crystals, specifically alkali-earth fluorides doped by Pb are characterized by three absorption bands: A (200–210 nm), B (160–170 nm) and C (150–160 nm). These bands are attributed to electron transitions from Pb2+ ions ground state 1S0 to excited states 3P1, 3P2 and 1P1 correspondingly. Excitation into all three bands gives rise to fluorescence, characterized by one broadband emission peaked, for example, in CaF2 at 235 nm at room temperature.

In accordance with our invention we quality control fluoride crystals by measuring Pb fluorescence intensity under excitation into its A-absorption band (200–210 nm).

Figure 14:
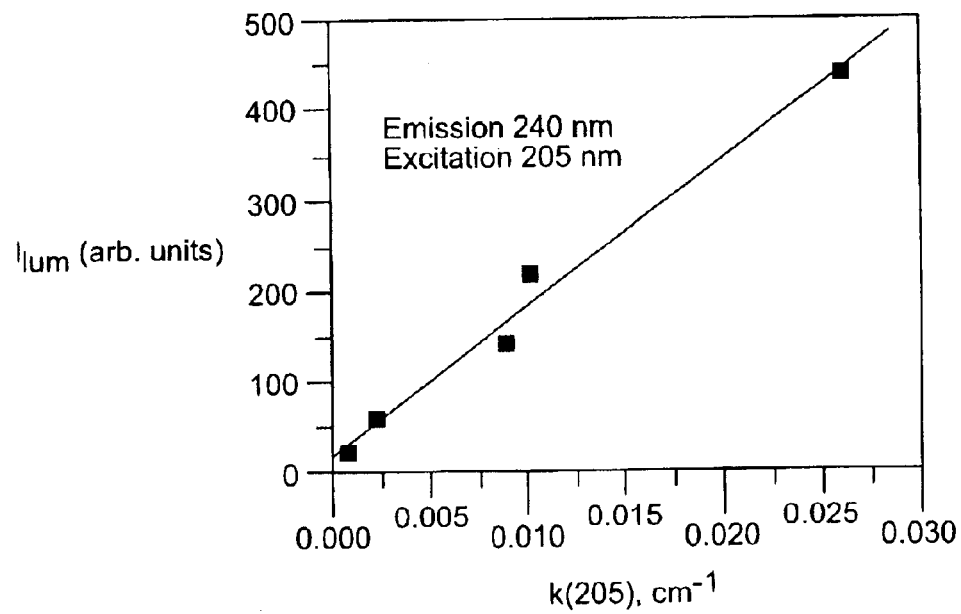
FIG. 14 is a plot of showing the linear relationship between Pb luminescence intensity (excitation 205 nm) and Pb absorption coefficient at 205 nm.

In the case of weak absorption of incident light by Pb impurity the luminescence intensity of Pb is proportional to Pb concentration $$Ilum \sim \epsilon(\lambda ex) * [Pb],$$

where $\epsilon(\lambda ex)$ is extinction coefficient at excitation wavelength $\lambda ex$, which has a meaning of absorption coefficient per unit of Pb concentration, designated as [Pb]. FIG. 14 illustrates linear relationship between Pb luminescence intensity Ilum under excitation 205 nm and Pb absorption coefficient k(205) at the same wavelength. Taking into consideration that $k(205)=\epsilon E(205)*[Pb]$, linear dependence in FIG. 14 confirms linear relationship between Ilum and [Pb]. Thus the Pb concentration in the crystal can be determined by comparison between Pb luminescence intensity of analyzable sample with corresponding luminescence intensity of some reference sample with known Pb concentration.

Figure 15:
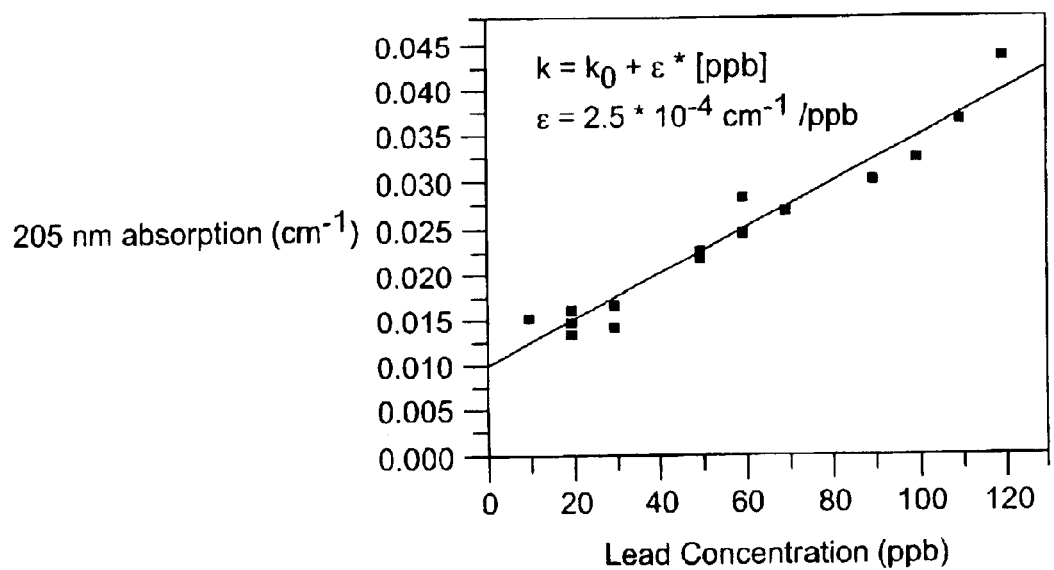
FIG. 15 is a plot of Pb absorption at 205 nm versus Pb concentration.

In Corning Incorporated French Patent Application No. 0116097 (Dec. 13, 2001) it was shown that for the CaF2 samples containing Pb more than 1 ppb, concentration of Pb can be determined basing on absorption data in the range 200–210 nm. We confirm this result by additional data in FIG. 15, where Pb absorption at wavelength 205 nm (A-band maximum) is plotted versus Pb content (chemical analysis data) for the set of CaF2 samples. From the slope of this linear dependence we obtain $\epsilon(205)=2.5*10-4$ cm−1/ppb. It should be noted that in order to evaluate Pb content in the range from 1 to 10 ppb, the sample length along optical pass is to be not less than 100 mm.

In Corning Incorporated French Patent Application No. 0116097 (Dec. 13, 2001) it was shown that absorption coefficient of Pb at C-band maximum (155 nm) is approximately 2.5 times higher than absorption coefficient at A-band maximum (205 nm). Basing on this relationship we can obtain extinction coefficient for C-band at 155 nm which is $\epsilon(155)=6.25*10-4$ cm−1/ppb.

Samples where Pb content was determined from crystal absorption data, were used for establishment the relationship between Pb luminescence intensity and Pb concentration data.

Figure 16A:
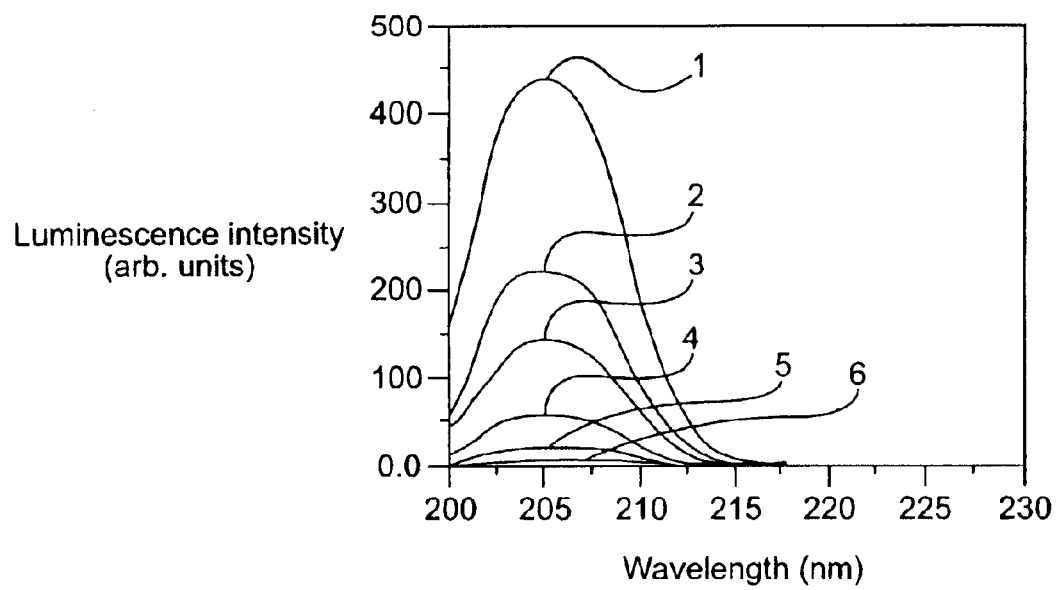
FIG. 16 is the luminescence excitation spectra for eight CaF2 crystal samples with different Pb content with curve numbers corresponding to sample numbers.
Figure 16B:
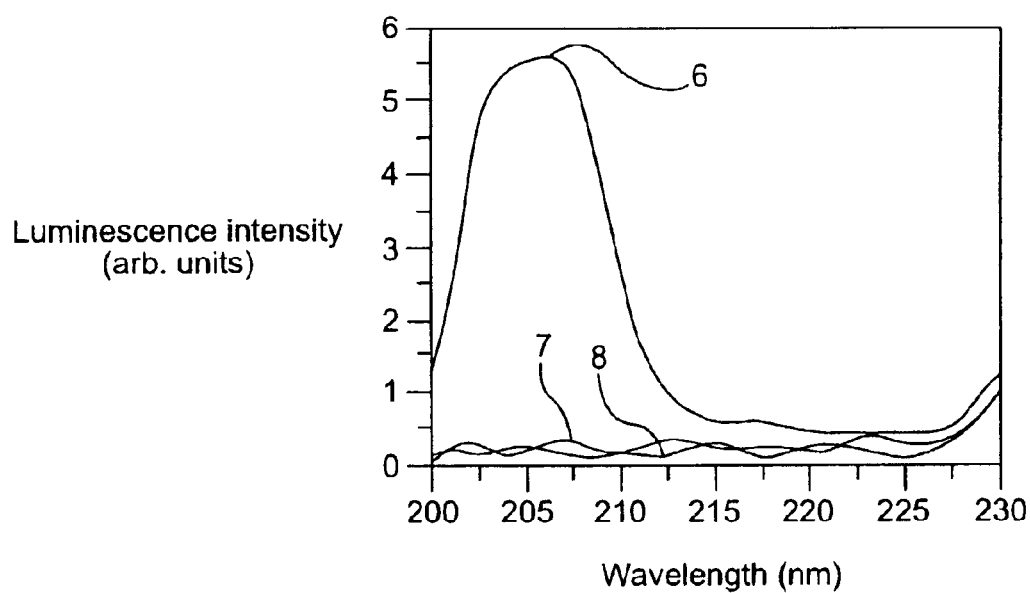

In FIGS. 16a–b there are shown Pb luminescence excitation spectra for eight CaF2 samples with different Pb content. Luminescence of sample 6 (curve 6) is shown in different intensity ranges (FIG. 16(a) and FIG. 16(b)). Luminescence signal of samples 7 (curve 7) and 8 (curve 8) doesn't exceed noise level and is out of detection limit.

Figure 17:
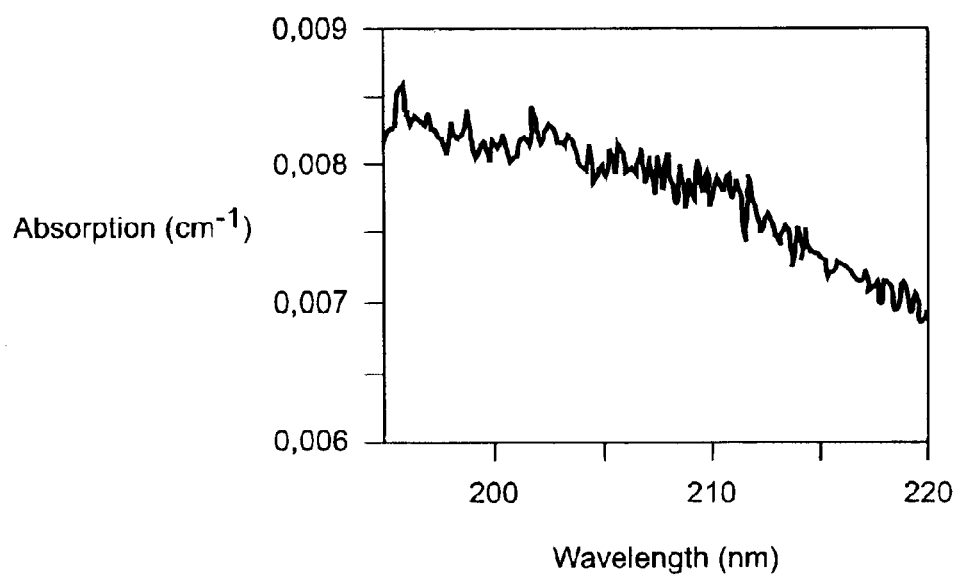
FIG. 17 is an absorption spectrum of sample 6 in the spectral range of A-absorption band (200 nm–210 nm) of Pb.
Figure 18:
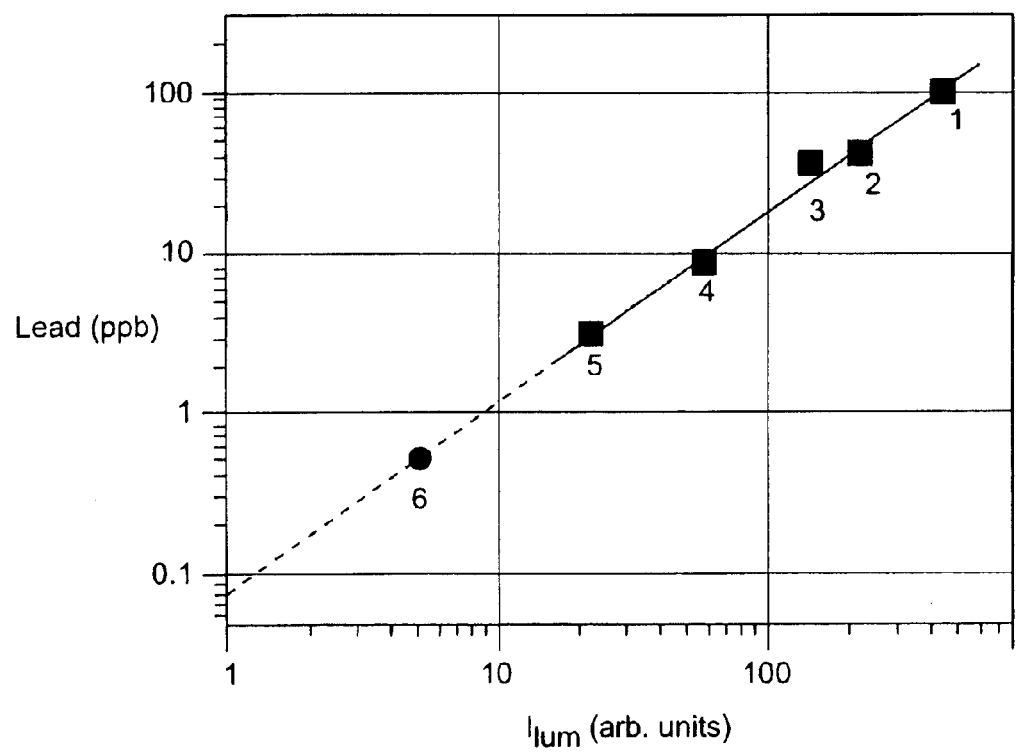
FIG. 18 is a plot relationship between Pb concentration and luminescence intensity.

Pb concentration in the samples 1–5 was determined on the basis of absorption data at 205 nm and extinction coefficient $\epsilon$ (205). So determined Pb concentration data for samples 1–5 were plotted versus Pb luminescence intensity for the same samples (see FIG. 18, square dots). The relationship between Pb concentration and luminescence intensity is well described by linear function (FIG. 18, solid line). The lowest Pb concentration possible to be measured by absorption method was 3 ppb (sample 5). As for the sample 6 it was possible to detect Pb in this sample only by luminescence method (FIG. 16(b), curve 6). For comparison, FIG. 17 illustrates absorption spectrum of the sample 6 in the spectral range of A-absorption band of Pb (200–210 nm). As it is seen no absorption band can be detected except noise. At the same time signal of Pb luminescence for the same sample 6 (FIG. 16(b), curve 6) exhibits a good signal-to noise ratio. This example illustrates high sensitivity of luminescence analysis compared to absorption one.

Extrapolating the linear dependence in FIG. 18 (solid line) into the range of low (<1 ppb) Pb concentrations we obtain linear relationship (FIG. 18, dashed line) between Pb concentration and Pb luminescence intensity in the range <1 ppb. And this Pb concentration range is available only for luminescence technique. Pb concentration in the sample 6 measured by luminescence method is equal to 0.6 ppb.

As follows from luminescence signal magnitude, with the help of a spectrofluorimeter 22 and using samples of the size about 10×10×5 mm it is possible to measure Pb concentration in fluoride crystals up to 0.1 ppb. So in comparison with absorption technique luminescence method provides 10 times more high sensitivity of Pb impurity analysis in fluoride crystals. For comparison Pb may also be analyzed by ICP-AES. However this method requires "wet chemistry" steps contaminating the sample, and the detection limit of this method doesn't exceed 1 ppm.

In Corning Incorporated French Patent Application No. 0116097 (Dec. 13, 2001) it was shown that in order to guarantee fluoride crystal transmission >99.0%/cm at 157 nm the absorption coefficient of Pb between 200 and 210 nm must be <0.0017 cm−1 (base 10). Inasmuch as Pb extinction coefficient is 2.5*10−4 cm−1/ppb at 205 nm, it means that Pb content should be <6.8 ppb. This value is close to detection limit of absorption analytical method but, as we have shown, is not a problem for luminescence analysis.

Except high sensitivity, another advantage of luminescence method compared to absorption technique is an ability to perform analysis in local places of crystal ingot, because the size of the sample used for luminescence measurements may be small enough (~10×10×5 mm). Whereas absorption technique needs long samples (50–100 mm) in order to provide high sensitivity and therefore gives information only about average Pb concentration along sample length. Such advantage of luminescence analysis is important because the distribution of impurity over crystal ingot is inhomogeneous and it is important to get information about local Pb concentration.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed is:

1. A method of detecting sub-ppm lead impurity levels in a below 200 nm transmitting optical calcium fluoride crystal said method comprising: providing a below 200 nm wavelength transmitting optical calcium fluoride crystal, providing a fluorescence spectrometer having a light source for producing a 200 to 210 nm selectable wavelength incident radiation and a detector for detecting excited luminescence light in the wavelength range of 210–260 nm produced by said incident radiation,
    exciting a first luminescence area of said crystal with said 200 to 210 nm selectable wavelength incident radiation and detecting with said detector excited 210 to 260 luminescence light produced from said crystal luminescence area by said 200 to 210 incident radiation to provide a lead ppb impurity level measurement less than 100 ppb.

2. A method as claimed in claim 1 wherein said light source is a lamp.

3. A method as claimed in claim 1, further comprising exciting a second luminescence area of said crystal to provide a second lead ppb impurity level measurement with said second luminescence area different from the first luminescence area.

4. A method as claimed in claim 1, further comprising exciting a plurality of luminescence areas of said crystal to provide a lead impurity level mapping of said crystal.

5. A method as claimed in claim 1, wherein exciting said luminescence area and detecting excited 210 to 260 nm luminescence light provides a measured lead impurity level less than 10 ppb.

6. A method as claimed in claim 1, wherein exciting said luminescence area and detecting excited 210 to 260 nm luminescence light provides a measured lead impurity level less than 1 ppb.

7. A method as claimed in claim 1, wherein exciting said luminescence area and detecting excited 210 to 260 nm luminescence light provides a measured lead impurity level less than 0.1 ppb.

8. A method of measuring below 1 ppm impurity levels in an optical fluoride crystal for transmitting below 200 nm wavelength of light, said method comprising,
    providing a fluorescence spectrometer for producing a selectable wavelength incident radiation greater than 200 nm and detecting excited luminescence light produced by the incident radiation,
    providing an optical fluoride crystal for transmitting below 200 nm wavelengths of light, said optical fluoride crystal containing an impurity at a contamination level less than 1 ppm,
    exciting said optical fluoride crystal with said fluorescence spectrometer selectable wavelength incident radiation and detecting excited luminescence light from the optical fluoride crystal impurity to provide a contaminant level measurement less than 50 ppb.

9. A method as claimed in claim 8 wherein said method provides a contaminant level measurement with a detection limit less than 10 ppb.

10. A method as claimed in claim 8 wherein said method provides a contaminant level measurement with a detection limit less than 1 ppb.

11. A method as claimed in claim 8 wherein said method provides a contaminant level measurement with a detection limit less than 0.1 ppb.

12. A method as claimed in claim 8 wherein said fluorescence spectrometer includes an optical waveguide and exciting said crystal includes transmitting said incident radiation through said optical waveguide to said crystal and detecting includes transmitting said excited luminescence light from said crystal through said optical waveguide.

13. A method as claimed in claim 8 including mapping a variation of said contaminant level in said fluoride crystal.

14. A method as claimed in claim 8 wherein said fluorescence spectrometer is calibrated with an optical fluoride crystal reference having a known contaminant level.

15. A method as claimed in claim 8, said method including measuring at least one luminescence intensity of said crystal.

16. A method of making a below 200 nm wavelength optical element, said method comprising:
    providing a below 200 nm wavelength transmitting optical fluoride crystal,
    providing a fluorescence spectrometer for producing a selectable wavelength incident radiation and detecting excited luminescence light produced by the incident radiation,
    exciting said optical fluoride crystal with said fluorescence spectrometer selectable wavelength incident radiation and detecting excited luminescence light from the optical fluoride crystal to provide a contaminant level measurement less than 50 ppb.,
    forming the optical fluoride crystal into a below 200 nm wavelength optical element having a less than 50 ppb measured contaminant level.

17. A method as claimed in claim 16, wherein providing a below 200 nm wavelength transmitting optical fluoride crystal comprises providing a calcium fluoride crystal with a below 200 nm transmission greater than 99%/cm and exciting said calcium fluoride crystal includes exciting with fluorescence spectrometer selectable wavelength incident radiation in the range of 200 to 210 nm and detecting excited luminescence light in the wavelength range of 210–260 nm to provide a lead contaminant level measurement less than 50 ppb.

18. A method as claimed in claim 16 including mapping a variation of said contaminant level in said crystal.

19. A method of making a below 200 nm wavelength transmitting optical fluoride crystal, said method comprising:
   providing a premelt calcium fluoride crystal solid,
   melting said premelt calcium fluoride crystal solid to form a calcium fluoride melt and growing a calcium fluoride crystal from said melt to provide an optical calcium fluoride crystal for transmitting below 200 nm wavelengths,
   providing a fluorescence spectrometer having a light source for producing a 200 to 210 nm selectable wavelength incident radiation and a detector for detecting excited luminescence light in the wavelength range of 210–260 nm produced by said incident radiation and measuring a lead contaminant level in calcium fluoride with said fluorescence spectrometer.

20. A method as claimed in claim 19, wherein measuring a lead contaminant level in calcium fluoride with said fluorescence spectrometer includes measuring the lead contaminant level in the premelt calcium fluoride crystal solid.

21. A method as claimed in claim 19, wherein measuring a lead contaminant level in calcium fluoride with said fluorescence spectrometer includes measuring the lead contaminant level in the calcium fluoride crystal grown from the calcium fluoride melt.

22. A method as claimed in claim 19, wherein said optical calcium fluoride crystal for transmitting below 200 nm wavelengths has a lead ppb excitation level less than 20.

23. A method as claimed in claim 22, said optical calcium fluoride crystal having a lead ppb excitation level less than 10.

24. A method as claimed in claim 22, said optical calcium fluoride crystal having a lead ppb excitation level less than 1.

25. A method as claimed in claim 22, said optical calcium fluoride crystal having a lead ppb excitation level less than 0.1.

26. A method as claimed in claim 22, said optical calcium fluoride crystal having a lead ppb excitation level less than 0.01.

* * * * *